United States Patent [19]
Hindsgaul et al.

[11] Patent Number: 6,013,634
[45] Date of Patent: *Jan. 11, 2000

[54] SOLID SUPPORT MATRICES CONTAINING A TOXIN BINDING OLIGOSACCHARIDE

[75] Inventors: Ole Hindsgaul, Edmonton, Canada; Ulf J. Nilsson, Lund, Sweden

[73] Assignee: Synsorb Biotech, Inc., Calgary, Canada

[ * ] Notice: This patent is subject to a terminal disclaimer.

[21] Appl. No.: 09/053,785

[22] Filed: Apr. 2, 1998

Related U.S. Application Data

[63] Continuation-in-part of application No. 08/746,393, Nov. 8, 1996, Pat. No. 5,846,943.

[51] Int. Cl.$^7$ .............................. A61K 31/70; C07H 15/00
[52] U.S. Cl. ................................ 514/25; 514/24; 514/42; 536/4.1; 536/17.9; 536/22.1; 536/29.1
[58] Field of Search .................................. 514/24, 25, 42; 536/4.1, 17.9, 22.1, 29.1

[56] References Cited

U.S. PATENT DOCUMENTS

| | | | |
|---|---|---|---|
| 4,415,733 | 11/1983 | Tayot | 536/53 |
| 4,923,980 | 5/1990 | Blomberg | 127/29 |
| 5,079,353 | 1/1992 | Ratcliff et al. | 536/18.2 |
| 5,484,773 | 1/1996 | Heerze et al. | 424/194.1 |
| 5,846,943 | 12/1998 | Hindsgaul et al. | 514/25 |

FOREIGN PATENT DOCUMENTS

| | | |
|---|---|---|
| 0 352 766 | 1/1990 | European Pat. Off. . |
| 0 606 925 | 7/1994 | European Pat. Off. . |
| 93/08209 | 4/1993 | WIPO . |
| 96/39189 | 12/1996 | WIPO . |

OTHER PUBLICATIONS

Bartlett, J.G., et al., "Antibiotic–Associated Pseudomembranous Colitis Due to Toxin–Producing Clostridia", *N. Engl. J. Med.*, 298:531–534 (1978).

Lyerly, D.M., "Epidemiology of *Clostridium difficile* Disease", *Clin. Microbiol. News*, 15:49–53 (1993).

Heerze, L.D., et al., "Oligosaccharide Sequences Attached to an Inert Support (SYNSORB) as Potential Therapy for Antibiotic–Associated Diarrhea and Pseudomembranous Colitis", *J. Infect. Dis.*, 169:1291–1296 (1994).

Spangler, B.D., "Structure and Function of Cholera Toxin and Related *Escherichia coli* Heat–Labile Enterotoxin", *Microbiological Reviews*, 56(4):622–647 (1992).

Edelman, R, et al., "Summary of the International Symposium and Workshop on Infections Due to Verocytotoxin (Shiga–like Toxin)–Producing *Escherichia coli*", J. Infect. Dis. 157:1102–1104 (1988).

Armstrong, G.D., et al., "Investigation of Shiga–like Toxin Binding to Chemically Synthesized Oligosaccharide Sequences", *J. Infect. Dis.*, 164:1160–1167 (1991).

Armstrong, G.D., et al., "A Phase I Study of Chemically Synthesized Verotoxin (Shiga–like Toxin) Pk–Trisaccharide Receptors Attached to Chromosorb For Preventing Hemolytic–Uremic Syndrome", *J. Infect. Dis.*, 171:1042–1045 (1995).

Karlsson, K.–A., "Animal Gylcosphingolipids as Membrane Attachment Sites for Bacteria", *Ann. Rev. Biochem.*, 58:309–350 (1989).

Fishman, P.H., "Gangliosides as Receptors for Bacterial Enterotoxins", *Adv. Lipid Res.*, 25:165–187 (1993).

Blomberg, L., et al., "Immobilization of Reducing Oligosaccharides to Matrices by a Glycosylamide Linkage", *J. Carbohydr. Chem.*, 12:265–276 (1993).

Hutchins, S.M., et al., "A Strategy for Urea Linked Diamine Libraries", *Tetrahedron Letters*, 36:2583–2586 (1995).

Weetal, et al., "Porous Glass for Affinity Chromatography Applications" In *Methods in Enzymology*, vol. XXXIV, (Jacoby, et al. Editors), Academic Press, New York (1974) pp. 59–72.

Dubois, et al., "Colorimetric Methods for Determination of Sugars and Related Substances", *Anal. Chem.*, 28:350–356 (1956).

Blanken and van de Eijnden, Biosynthesis of Terminal Gal$\alpha$1–3Gal$\beta$1–4GlcNAc Oligosaccharide Sequences on Glycoconjugates, *J. Biol. Chem.*, 260:12927–12934 (1985).

Palcic, et al., The Use of Hydrophobic Synthetic Glycosides as Acceptors in Glycosyltransferase Assays, *Glycconj. J.*, 5:49–63 (1988).

*Primary Examiner*—Howard C. Lee
*Attorney, Agent, or Firm*—Burns, Doane, Swecker & Mathis, LLP

[57] ABSTRACT

Disclosed are novel solid support matrices having a toxin-binding oligosaccharide covalently attached to a solid support through a linking arm which has at least 5 atoms separating the oligosaccharide from the solid support. The disclosed solid support matrices are useful for neutralizing toxins from disease-causing microorganisms.

10 Claims, 5 Drawing Sheets

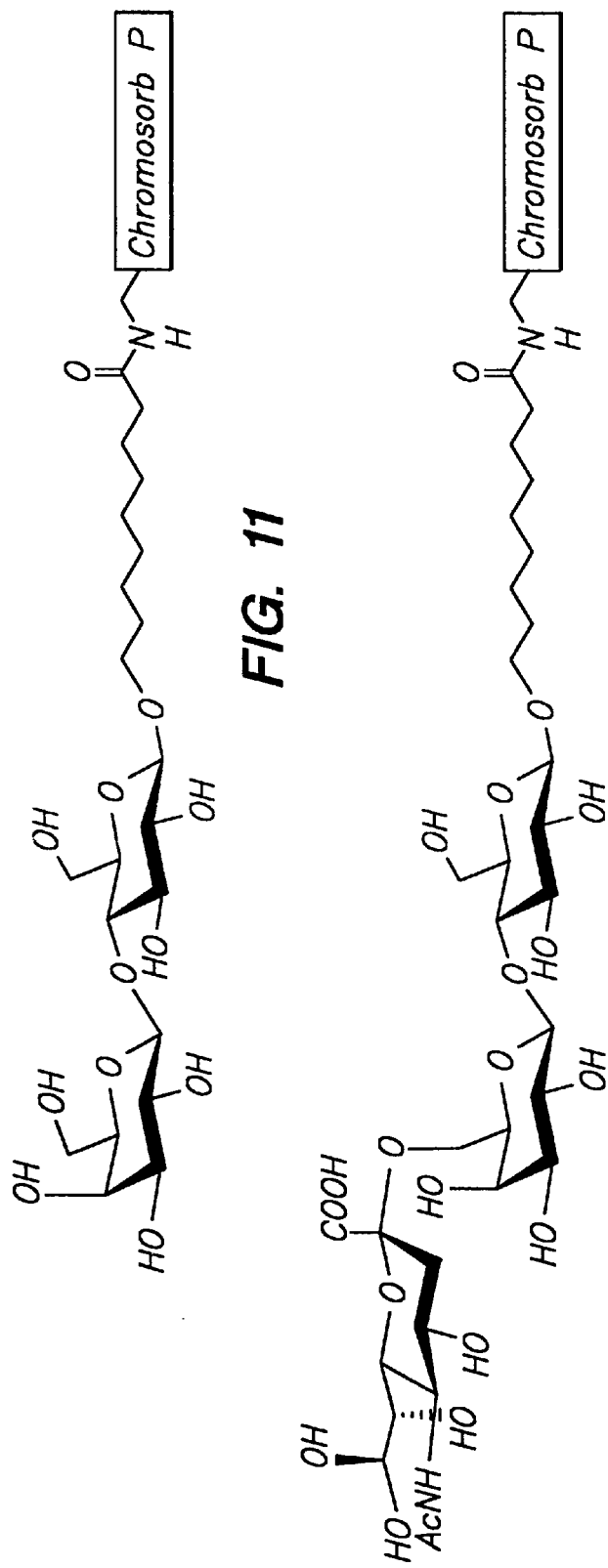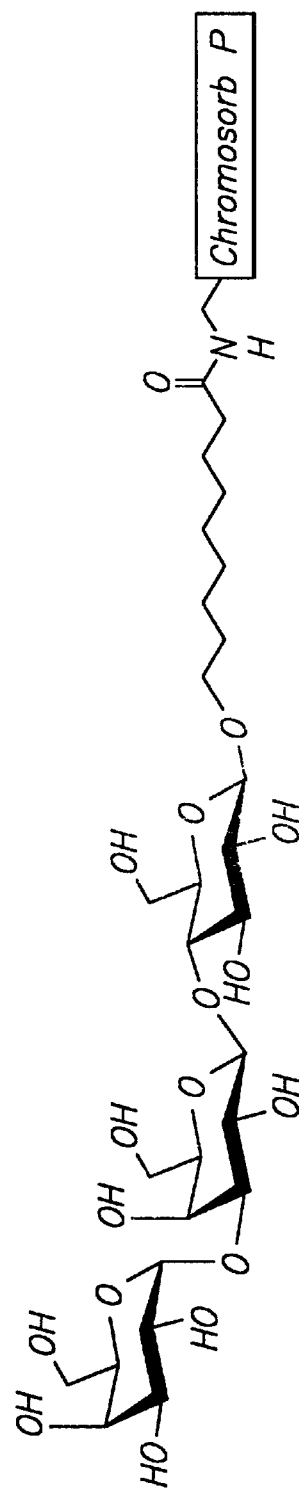
FIG. 11
FIG. 12
FIG. 13

FIG. 14

SOLID SUPPORT MATRICES CONTAINING A TOXIN BINDING OLIGOSACCHARIDE

CROSS-REFERENCE TO RELATED APPLICATIONS

This application is a continuation-in-part of U.S. patent application Ser. No. 08/746,393, filed Nov. 8, 1996 now U.S. Pat. No. 5,846,943 which application is incorporated herein by reference in its entirety.

BACKGROUND OF THE INVENTION

Field of the Invention

This invention is directed to novel solid support matrices containing an oligosaccharide which binds toxins from disease-causing microorganisms. More specifically, the matrix aspects of this invention relate to novel solid support matrices having a toxin-binding oligosaccharide covalently attached to a solid support through a linking arm which has at least 5 atoms separating the oligosaccharide from the solid support.

Binding of toxins from disease-causing microorganism is achieved both in vitro and in vivo. When binding is achieved in vivo, the matrices described herein are preferably delivered via a pharmaceutical composition. Accordingly. this invention is also directed to pharmaceutical compositions comprising a solid support matrix as described herein.

References

The following publications, patents and patent applications are cited in this application as superscript numbers:

1. Bartlett, J. G., et al., "Antibiotic-Associated Pseudomembranous Colitis Due to Toxin-Producing Clostridia", *N. Engl. J. Med.*, 298:531–534 (1978).
2. Lyerly, D. M., "Epidemiology of *Clostridium difficile* Disease", *Clin. Microbiol. News*, 15:49–53 (1993).
3. Heerze, L. D., et al., "Oligosaccharide Sequences Attached to an Inert Support (SYNSORB) as Potential Therapy for Antibiotic-Associated Diarrhea and Pseudomembranous Colitis", *J. Infect. Dis.*, 169:1291–1296 (1994).
4. Heerze, L. D., et al., U.S. Pat. No. 5,484,773, for "Treatment of Antibiotic Associated Diarrhea", issued Jan. 16, 1996.
5. Spangler, B. D., "Structure and Function of Cholera Toxin and Related *Escherichia coli* Heat-Labile Enterotoxin", *Microbiological Reviews*, 56(4):622–647 (1992).
6. Edelman, R, et al., "Summary of the International Symposium and Workshop on Infections Due to Verocytotoxin (Shiga-like Toxin)-Producing *Escherichia coli*", J. Infect. Dis. 157:1102–1104 (1988).
7. Armstrong, G. D., et al., "Investigation of Shiga-like Toxin Binding to Chemically Synthesized Oligosaccharide Sequences", *J. Infect. Dis.*, 164:1160–1167 (1991).
8. Armstrong, G. D., et al., "A Phase I Study of Chemically Synthesized Verotoxin (Shiga-like Toxin) Pk-Trisaccharide Receptors Attached to Chromosorb For Preventing Hemolytic-Uremic Syndrome", *J. Infect. Dis.*, 171:1042–1045 (1995).
9. Rafter, et al., U.S. patent application Ser. No. 08/669,004, for "Treatment of Bacterial Dysentery" filed Jun. 21, 1996 now U.S. Pat. No. 5,849,714.
10. Karlsson, K.-A., "Animal Gylcosphingolipids as Membrane Attachment Sites for Bacteria", *Ann. Rev. Biochem.*, 58:309–350 (1989).
11. Fishman, P. H., "Gangliosides as Receptors for Bacterial Enterotoxins", *Adv. Lipid Res.*, 25:165–187 (1993).
12. Blomberg. L., U.S. Pat. No. 4,923,980, for "Process for the Manufacture of a Gel Product", issued May 8, 1990.
13. Blomberg, L., et al., "Immobilization of Reducing Oligosaccharides to Matrices by a Glycosylamide Linkage", *J. Carbohydr. Chem.*, 12:265–276 (1993).
14. Hutchins, S. M., et al., "A Strategy for Urea Linked Diamine Libraries", *Tetrahedron Letters*, 36:2583–2586 (1995).
15. Ratcliffe, et al., U.S. Pat. No. 5,079,353, for "Sialic Acid Glycosides Antigens Immuno-Adsorbents and Methods for Their Preparation", issued Jan. 7, 1992
16. Weetal, et al., "Porous Glass for Affinity Chromatography Applications" in *Methods in Enzymology*, Vol. XXXIV, (Jacoby, et al. Editors), Academic Press, New York (1974) pp. 59–72.
17. Dubois, et al., "Colorimetric Methods for Determination of Sugars and Related Substance", *Anal. Chem.*, 28:350–356 (1956)
16. Blanken and van de Eijnden, "Biosynthesis of Terminal Galα1-3Galβ1-4GlcNAc Oligosaccharide Sequences on Glycoconjugates, *J. Biol. Chem.*, 260: 12927–12934 (1985)
17. Palcic, et al., "The Use of Hydrophobic Synthetic Glycosides as Acceptors in Glycosyltransferase Assays, *Glycconj. J.*, 5:49–63 (1988)

All of the above publications, patents and patent applications are herein incorporated by reference in their entirety to the same extent as if each individual publication, patent or patent application was specifically and individually indicated to be incorporated by reference in its entirety.

State of the Art

Toxins produced by bacteria and other organisms are known to cause a number of human diseases, including many diarrheal diseases. For example, toxin A, produced by the anaerobic organism *Clostridum difficile*, is the major causative agent of antibiotic-associated diarrhea ("*C. difficile* associated diarrhea" or "CDAD") and pseudomembranous colitis ("PMC").[1-4] Similarly, heat-labile enterotoxin ("LT"), secreted by certain enterotoxigenic strains of *Escherichia coli*, has been identified as one of the causative agents of bacterial-induced traveller's diarrhea.[5] In addition, the shiga-like toxins ("SLT"), produced by enterohemorrhagic *E. coli*, are known to be responsible for hemorrhagic colitis and hemolytic-uremic syndrome.[6-8] Shiga-like toxins are also associated with bacteria-caused dysentery.[9] And, of significant importance, cholera toxin ("CT"), produced by *Vibrio cholerae*, has been identified as the causative agent of the severe diarrheal disease, cholera.[5]

Many of these toxins from disease-causing microorganisms are known to bind to oligosaccharide receptors on host cells as an initial step in the pathological development of the associated disease condition.[10,11] Accordingly, one approach reported in the literature for diagnosing and treating such toxin-mediated diseases is to adsorb the toxin from a toxin-containing sample or from the intestine using, for example, an oligosaccharide receptor analog which binds the toxin immobilized on an inert solid support.

For example, Heerze et al. have reported that *Clostridium difficile* toxin A binds to certain synthetic oligosaccharide sequences covalently attached to an inert solid support through a linking arm of at least one carbon atom with specific exemplification of the —O(CH$_2$)$_8$C(O)— linker arm.[3] These oligosaccharide-containing solid supports are reported to effectively neutralize toxin A activity in stool samples from patients with *C. difficile* associated diarrhea.

Additionally, Heerze et al. have disclosed pharmaceutical compositions containing an oligosaccharide sequence covalently attached to a pharmaceutically acceptable solid, inert support through a non-peptidyl compatible linker arm, wherein the oligosaccharide sequence binds toxin A.[4] Also disclosed are methods of treating diarrhea mediated by toxin A using such compositions.

Similarly, Armstrong et al. have reported that shiga-like toxins, i.e., SLT-I and SLT-II/IIc, bind to certain synthetic αGal(1-4)βGal sequences covalently attached to an inert solid support through a —O(CH$_2$)$_8$C(O)— linker arm.[7,8]

Although various oligosaccharide-containing solid support matrices are known in the art, conventional methods for preparing these matrices involve laborious chemical synthesis of a complex oligosaccharide carrying a functionalized linking arm suitable for coupling the oligosaccharide to a solid support (e.g., an —O(CH$_2$)$_8$C(O)— linking arm). The synthesis of such oligosaccharides generally requires the selective protection and deprotection of various functional groups on the oligosaccharide (e.g., hydroxyl groups) in order to synthesize the desired sugar structure while allowing appropriate linkage to the solid support. Such complex synthetic procedures are quite laborious with overall low yields due to the rather high number of individual reaction steps. As is apparent, the combination of complex chemistry with overall low yields hampers the widespread commercial development and use of these matrices.

In contrast, Blomberg et al. have disclosed a method for matrix formation which couples a reducing oligosaccharide to the amine group of a spacing arm attached to a solid support followed by N-acylation to form a glycosylamide linkage.[12,13] The methods described by Blomberg, et al.[13] provide, however, for a limited class of hydrophilic hydroxyl containing linking arms and, accordingly, do not permit linking arms of selected hydrophobicity/hydrophilicity.

In view of the above, there is an ongoing need to provide for linkage of toxin binding oligosaccharides to solid supports through linking arms wherein the preparation of such linking arms is synthetically facile and permits a wide range of different chemistries.

SUMMARY OF THE INVENTION

This invention provides for novel solid support matrices which are useful for diagnosing or neutralizing various toxins from disease-causing microorganisms. The solid support matrices of this invention are characterized both by the relative ease of synthesis and the broad range of linking arms which can be prepared.

Accordingly, in one of its composition aspects, this invention is directed to a solid support matrix represented by the formula:

$$SS-[R^1-X-\overset{\overset{W}{\|}}{C}-Y(R^2X')_pR^2NR^3-Z]_n$$

wherein SS is a solid support;

R$^1$ is selected from the group consisting of a covalent bond and a hydrocarbylene group having from 1 to about 20 carbon atoms;

R$^2$ is a hydrocarbylene group of from 2 to 20 carbon atoms;

each X' is independently selected from the group consisting of —O— and >NR$^4$ wherein each R$^4$ is independently selected from hydrogen, —R$^2$NH$_2$ or —R$^2$NR$^3$Z wherein R$^2$ is as defined above;

R$^3$ is selected from the group consisting of hydrogen and —C(O)R$^5$ wherein R$^5$ is selected from the group consisting of hydrogen and hydrocarbyl of from 1 to 20 carbon atoms;

W is selected from oxygen or sulfur;

X is selected from the group consisting of —NH—, —O— and —S—;

Y is selected from the group consisting of —NH—, —O— and —S—;

Z is toxin-binding oligosaccharide;

p is an integer of from 0 to 50 or more; and n is an integer such that the matrix has a loading level of the toxin-binding oligosaccharide of from about 0.001 to about 2000 μmols per gram of solid support wherein the total number of atoms in separating the solid support from the toxin-binding oligosaccharide is at least 5.

Particularly preferred matrices of this invention include those where X and Y are NH, W is oxygen, p is 0 and R$^2$ is an alkylene group of from 4 to 10 carbon atoms. Such preferred matrices are represented by the formula:

$$SS-[R^1-NH\overset{\overset{O}{\|}}{C}NH-R^6-NR^3-Z]_n$$

wherein SS, R$^1$, R$^3$, Z and n are as defined above and R$^6$ is an alkylene group of from 4 to 10 carbon atoms.

In another aspect, the invention provides a pharmaceutical composition useful for in vivo treatment of a toxin-mediated disease in a mammal, which composition comprises a solid support matrix described above and a pharmaceutically acceptable carrier suitable for oral administration, wherein the matrix is capable of being eliminated from the gastrointestinal tract.

BRIEF DESCRIPTION OF THE DRAWINGS

FIGS. 11–13 illustrate the chemical structure of SYNSORB 16, SYNSORB 89 and SYNSORB Cd respectively.

FIG. 14 demonstrates the neutralization of purified toxin A hemagglutination activity using solid support matrices containing an oligosaccharide.

DETAILED DESCRIPTION OF THE INVENTION

Figure 1:
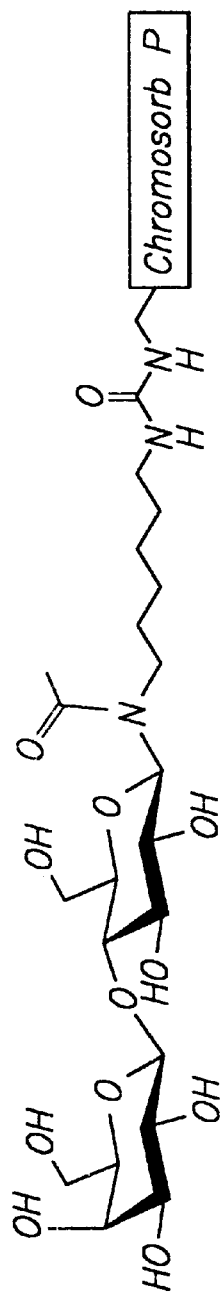
FIGS. 1–10 illustrate the chemical structures of various oligosaccharides attached to solid support matrices as described in Table 1.

As discussed above, this invention is directed, in part, to novel solid support matrices having covalently linked thereto through a linking arm an oligosaccharide which binds toxins from disease-causing microorgansims. However, prior to discussing this invention in further detail, the following terms will first be defined.

Definitions

As used herein, the following terms have the following meanings unless expressly stated to the contrary.

The term "a toxin-binding reducing oligosaccharide" refers to oligosaccharide structures which bind toxins expressed by bacterial or other microbial sources which oligosaccharides are in their reduced form. That is to say that the anomeric carbon atom of the reducing sugar is presented in an unprotected form as the —OH group. Examples of oligosaccharides which bind to toxins are well known in the art and are disclosed, for example, by Heerze, et al.[3,4] and Armstrong, et al.[7,8] Such oligosaccharides preferably contain from 2 to 8 saccharide units and more preferably from 2 to 4 saccharide units.

Such saccharide units include, by way of example, all natural and synthetic derivatives of glucose, galactose., N-acetylglucosamine, N-acetylgalactosamine, fucose, sialic acid, 3-deoxy-D,L-octulosonic acid, and the like. The saccharide units may be in either their pyranose or furanose form. Preferably, the saccharide units are in their pyranose form. Additionally, all saccharide units described herein are in their D form except for fucose which is in its L form.

The term "alkyl" refers to straight- or branched-chain alkyl groups having at least 1 carbon atom and preferably from 1 to 10 carbon atoms. Typical alkyl groups include, by way of example only, methyl, ethyl, n-propyl, iso-propyl, n-butyl, sec-butyl, n-decyl and the like.

The term "alkoxy" refers to the group —O-alkyl where alkyl is as defined above. Typical alkoxy groups include, by way of example only, methoxy, ethoxy, n-propoxy, iso-propoxy, n-butoxy, sec-butoxy, n-decoxy and the like.

The term "alkylene" refers to straight- or branched-chain alkylene groups having at least 1 carbon atom and preferably from 1 to 10 carbon atoms. Typical alkylene groups Lnclude, by way of example only, methylene (—CH$_2$—), ethylene (—CH$_2$CH$_2$—), propylene (—CH$_2$CH$_2$CH$_2$—), iso-propylene (—CH(CH$_3$)CH$_2$—), n-butylene (—CH$_2$CH$_2$CH$_2$CH$_2$—), sec-butylene (—CH(CH$_2$CH$_3$)CH$_2$—) ancl the like.

The term "alkenyl" refers to straight- or branched-chain alkenyl groups having at least 2 carbon atoms, preferably from 2 to 10 carbon atoms, and at least 1 point of double bond unsaturation. Typical alkenyl groups include, by way of example only ethenyl (—CH═CH$_2$), 1-propenyl (—CH═CHCH$_3$), 2-propenyl (—CH$_2$CH═CH$_2$), 2-butenyl (—CH$_2$CH═CHCH$_3$) and the like. It being understood that all isomers, e.g., cis and trans isomers, are included within this definition.

The term "alkenylerie" refers to straight- or branched-chain alkenylene groups having at least 2 carbon atoms, preferably from 2 to 10 carbon atoms, and at least 1 point of double bond unsaturation. Typical alkenylene groups include, by way of example only, ethenylene (—CH═CH—), 1-propenylene (—CH═CHCH$_2$—), 2-propenylene (—CH$_2$CH═CH—), 2-butenylene (—CH$_2$CH═CHCH$_2$—) and the like. It being understood that all isomers, e.g., cis and trans isomers, are included within this definition.

The term "alkynyl" refers to straight- or branched-chain alkynyl groups having at least 2 carbon atoms, preferably from 2 to 10 carbon atoms, and at least 1 point of triple bond unsaturation. Typical alkynyl groups include, by way of example only, ethynyl (—C≡CH), propargyl (—CH$_2$C≡CH) and the like.

The term "alkynylene" refers to straight- or branched-chain alkynylene groups having at least 2 carbon atoms, preferably from 2 to 10 carbon atoms, and at least 1 point of triple bond unsaturation. Typical alkynylene groups include, by way of example only, ethynylene (—C≡C—), propargylene (—CH$_2$C≡C—) and the like.

The term "aryl" refers to unsaturated aromatic carbocyclic groups preferably of from 6 to 14 carbon atoms having a single ring or multiple condensed rings which are optionally substituted with from 1 to 3 substituents selected from the group consisting of halo, nitro, cyano, alkyl, alkoxy, aryl, trihalomethyl, and the like. Examples of suitable aryl groups include phenyl, p-nitrophenyl, naphthyl and the like.

The term "arylene" refers to unsaturated aromatic carbocyclic groups of from 6 to 14 carbon atoms having a single ring or multiple condensed rings and two points of linkage which are optionally substituted with from 1 to 2 substituents selected from halo, nitro, cyano, alkyl, alkoxy, trihalomethyl, and the like. Examples of arylene groups include 1,4-phenylene (e.g.,

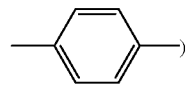

and the like. It being understood that all possible points of linkage are included within the term arylene (e.g., 1,4-phenylene, 1,3-phenylene, and the like).

The term "cycloalkyl" refers to cyclic alkyl groups of from 3 to 12 carbon atoms having a single cyclic ring or multiple condensed rings which can be optionally substituted vith from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like. Preferred cycloalkyl groups are single ring systems of from 3 to 8 carbon atoms.

The term "hydrocarbyl" refers to monovalent radicals comprising only carbon and hydrogen which include, by way of example only, alkyl, alkenyl, alkynyl, aryl, cycloalkyl, and the like.

The term "hydrocarbylene" refers to divalent radicals comprising only carbon and hydrogen which include, by way of example only, alkylene, alkenylene, alkynylene, arylene groups, and the like.

The term "linking arm" or "spacing arm" refers to the chemical group which covalently attaches the oligosaccharide to the solid support. The number of atoms in the linking arm separating the oligosaccharide and the solid support is determined by adding each of the linear atoms in the

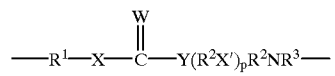

group. That is to say that the linear atoms comprise the sum of atoms in $R_1$ (non-branched atoms only), X, X', Y, $R^2$ (non-branched atoms only), plus 2 (i.e., the carbon and nitrogen atoms in the linear chain).

The term "oxyalkylene unit" refers to an ether moiety having the general formula: —$R^b$O—, wherein $R^b$ is an alkylene group, preferably of from 2 to 6 carbon atoms.

The term "poly(alkylene amine)" refers to a polymer or oligomer having the general formula: —($R^a$NH)$_c$—, wherein $R^a$ is an alkylene group, preferably of from 2 to 6 carbon atoms, and c is an integer greater than 1 and preferably about 12 or less. When referring to the number of alkylene amine units in a particular poly(alkylene amine) compound, it is to be understood that this number refers to the average number of alkylene amine units in such compounds unless expressly stated to the contrary. A mono (alkylene amine) group contains 1 alkylene amine unit. Examples of poly(alkylene amines) include, for instance, polyethyleneamines [e.g., —(CH$_2$CH$_2$NH)$_z$— where z is an integer from 2 to 12].

The term "poly(oxyalkylene)" refers to a polymer or oligomer having the general formula: —$(R^bO)_d$—, wherein $R^b$ is an alkylene group, preferably of from 2 to 6 carbon atoms, and d is an integer greater than 1 and typically about 50 or less. When referring to the number of oxyalkylene units in a particular poly(oxyalkylene) compound, it is to be understood that this number refers to the average number of oxyalkylene units in such compounds unless expressly stated to the contrary. A mono(oxyalkylene) group contains 1 oxyalkylene unit.

The term "solid support" refers to an inert, solid material to which an oligosaccharide may be bound via a linking arm. When used in vivo, the solid support will be biocompatible and pharmaceutically acceptable. Suitable solid supports include, by way of example only, silica, including synthetic silicates, such as porous glass; biogenic silicates, such as diatomaceous earth; silicate-containing minerals, such as kaolinite; synthetic polymers, such as polystyrene, polypropylene, etc.; polysaccharides such as dextrans, celluloses (CMC), alginates, chitins, and chitosans; and the like.

Preferred solid support materials for use in this invention are silica supports which have been silylaminated with a ω-aminoalkyltrialkoxysilane using conventional procedures. Suitable ω-aminoalkyltrialkoxysilanes include, for example, 3-aminopropyltriethoxysilane, 4-aminobutyltriethoxysilane and the like. A particularly preferred silica for use in such silylamination reactions is silica sold commercially under the tradename Chromosorb P™ by Manville Corp., Denver, Colo.

The term "antibiotic-associated bacterial diarrhea" refers to the condition wherein antibiotic therapy disturbs the balance of the microbial flora of the gut, allowing pathogenic organisms such as Clostridium difficile to flourish. These organisms cause diarrhea. Antibiotic-associated bacterial diarrhea includes such conditions as C. difficile associated diarrhea (CDAD) and pseudomembranous colitis (PMC).

The term "biocornpatible" refers to chemical inertness with respect to human tissues or body fluids. Biocompatible materials are non-sensitizing.

The term "cholera" refers to an acute epidemic infectious disease caused by Vibrio cholerae, wherein a soluble toxin elaborated in the intestinal tract by the Vibrio alters the permeability of the mucosa, causing a profuse watery diarrhea, extreme loss of fluid and electrolytes, and a state of dehydration and collapse, but no gross morphologic change in the intestinal mucosa.

The term "cholera toxin" refers to an enterotoxin of V. cholerae which initiates cholera and related conditions. This toxin has a lectin-like activity.

The terms "heat-labile toxin" or "LT" refer to an enterotoxin of enterotoxigenic E. coli which initiates traveller's diarrhea and related conditions. This toxin has a lectin-like activity.

The term "pseudoriembranous colitis" (PMC), also know as pseudomembranous enterocolitis or enteritis, refers to the inflammation of the mucous membrane of both small and large intestine with the formation and passage of psudomembranous material (composed of fibrin, mucous, necrotic epithelial cells and leukocytes) in the stools.

The term "toxin A" refers to an enterotoxin of Clostridium difficile which initiates CDAD and related conditions. This toxin has a lectin-like activity.

The term "traveller's diarrhea" refers to diarrhea of sudden onset, often accompanied by abdominal cramps, vomiting and fever that occurs sporadically in traveller's, usually during the first week of a trip. This diarrhea is most commonly caused by enterotoxigenic E. coli.

B. General Synthetic Procedures

The oligosaccharide-containing solid support matrices of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Oligosaccharide-containing solid support matrices of this invention may be prepared by contacting functionalized solid support materials of the formula:

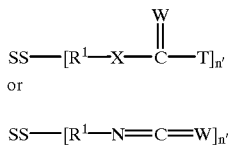

with a linking reagent of the formula HY—$(R^2X')_pR^2NH_2$ under conditions to form an amino-functionalized solid support material of the formula:

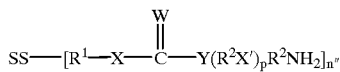

wherein SS, W, X, X', Y, $R^1$, $R^2$, and p are as defined above; T is selected from the group consisting of halogen and —$OR^7$ wherein $R^7$ is alkyl, haloalkyl, or aryl; n' is an integer such that the matrix has a loading level of the $R^1XC(=W)T$ or $R^1$—N=C=W functional group of from about 0.001 to about 2000 μmols per gram of matrix; and n" is an integer such that the amino-functionalized solid support material has a loading of amino groups of from about 0.001 to about 2000 μmols per gram.

Preferably, this reaction is conducted using an excess of the linking reagent based on the $R^1XC(=W)T$ or $R^1$—N=C=W functional groups in order to minimize or prevent cross-linking of the solid support. More preferably, from about 2 to about 50 molar equivalents of the linking reagent will be employed in the reaction based on the $R^1XC(=W)T$ or $R^1$—N=C=W functional groups. When T is a halo group, the reaction is preferably conducted in the presence of at least one molar equivalent, based on the linking reagent, of a suitable tertiary amine, such as diisopropylethylamine, triethylamine, pyridine and the like, to scavenge the acid generated by the reaction.

This reaction will generally be conducted at a temperature ranging from about –70° C. to about 70° C., in an essentially anhydrous inert diluent such as dimethylformamide, acetonitrile and the like, for about 1 to about 24 hours. After completion of the reaction, the amino-functionalized solid support material is recovered by conventional methods, such as filteration, centifugation and the like, and the recovered material is optionally washed one or more times with an inert diluent, such as dimethylformamide, water, methanol, dichloromethane and the like, to remove unreacted excess linking reagent and other soluble materials.

The functionalized solid support materials employed in this invention are well known in art and can be prepared by conventional procedures. For example, such material can be prepared from a solid support containing an amino, hydroxyl or thiol functional group by reaction of the solid support with a bifunctional reagent of the formula: L—C(=W)T wherein T and W are as defined above and L is a suitable leaving group, such as a halogen or —$OR^8$ wherein $R^8$ is an alkyl, haloalkyl or aryl group (including optionally substituted aryl groups). Suitable conditions for preparing a functionalized solid support using p-nitrophenyl chloroformate are described, for example, by S. M. Hutchins et al. in *Tetrahedron Letters.*[14]

Representative bifunctional reagents suitable for preparing functionalized solid support materials include, for example, alkyl haloformates, such as methyl chloroformate, methyl bromoformate, ethyl chloroformate, n-propyl chloroformate and the like, haloalkyl haloformates, such as trichloromethyl chloroformate (diphosgene); aryl haloformates, such as phenyl chloroformate p-chlorophenyl chloroformate, p-nitrophenyl chloroformate and the like; phosgene; thiophosgene; and other suitable phosgene and thiophosgene equivalents. Such bifunctional reagents are well known in the art and are typically commercially available.

The linking reagents employed in this invention are either known compounds or can be prepared from known compounds by conventional procedures. The linking reagent will typically contain a hydroxyl, thiol or primary amino functional group at or near one terminus of the reagent backbone and one or more primary amino groups at or near the opposite end of the reagent. In those cases where the reagent contains a hydroxyl or thiol functional group, it may be preferable to protect or block the primary amino group(s) in the reagent to allow the hydroxyl or thiol group to selectively react with the functionalized solid support material. When necessary, primary amino groups can be protected using conventional protecting or blocking groups, such as Cbz, t-boc, etc., which are well known to those skilled in the art.

A preferred group of linking reagents for use in this invention are alkylene diamines of the formula: $H_2N—R^9—NH_2$, wherein $R^9$ is an alkylene group having 2 to about 20 carbon atoms. Representative examples of such alkylene diamines include 1,4-diaminobutane (n-butylenediamine), 1,5-diaminopentane, 1,6-diaminohexane, 1,8-diaminooctane, and the like. Particularly preferred alkylene diamines are 1,4-diaminobutane and 1,6-diaminohexane.

Another preferred group of linking reagents are polyoxyalkylene diamines of the formula: $H_2N—(R^{10}O)_{p'}R^{10}—NH_2$, wherein $R^{10}$ is an alkylene group having 2 to about 3 carbon atoms and p' is an integer ranging from 1 to about 50. Preferred polyoxyalkylene diamines include 1,8-diamino-3,6-dioxaoctane and 1,11-diamino-3,6,9-trioxaundecane.

Still another preferred group of linking reagents are polyalkylene polyamines of the formula: $H_2N—(R^{11}NH)_{p''}—H$, wherein $R^{11}$ is an alkylene group having 2 to about 20 carbon atoms and p" is an integer ranging from 2 to about 20. Examples of suitable polyalkylene polyamines include diethylenetriamine, dipropylenetriamine, diisopropylenetriamine, dibutylenetriamine, triethylentetraamine, tetraethylenepentaamine and the like. Particularly preferred polyalkylene polyamines are di-, tri-, and tetra-ethylene amines.

The amino-functionalized solid support material prepared as described above is then coupled to a toxin binding reducing oligosaccharide to provide an oligosaccharide-containing solid support matrix of the formula:

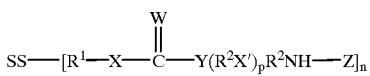

$$SS—[R^1—X—C(=W)—Y(R^2X')_pR^2NH—Z]_n$$

wherein SS, W, X, X', Y, Z, $R^1$, $R^2$, n, and p are as defined above.

This reaction is preferably conducted by contacting the amino-functionalized solid support material with about 1 to about 1000 molar equivalents (preferably 74), based on the primary amino groups in the linking arm, of the toxin binding reducing oligosaccharide under conditions as described by Blomberg, et al.[12,13] Preferably, a catalytic amount of acetic acid or a similar acid is employed in this reaction.

Preferably, this reaction is conducted in an inert diluent, such as methanol, ethanol and the like, at a temperature ranging from about 20° C. to about 100° C. The reaction is generally complete in about 12 to about 72 hours. Upon reaction completion, the product is recovered by conventional methods such as filtration, centrifugation, etc.

The toxin binding reducing oligosaccharides employed in this invention are either commercially available sugars (e.g., lactose) or can be prepared by conventional procedures which are well known to those skilled in the art. For example, such oligosacchairides can be prepared by enzymatic methods or by total chemical synthesis using known methodologies. See, for example, Ratcliffe, et al.[15]

Optionally, the glycosylamine linkage connecting the oligosaccharide and the linking arm can be acylated to form a glycosylamide linkage using the procedures described by Blomberg, et al.[12,13]

Preferred acylating agents for use in this reaction are those having the formula: $R^{12}C(O)—L'$, wherein $R^{12}$ is preferably a hydrocarbyl group having from 0 (i.e., formate) to about 20 carbon atoms (more preferably from 0 to 8 carbon atoms), and L' is a suitable leaving group. Typically, the leaving group, L', will be a halide, e.g., chloride or bromide; or a carboxylate group having the formula: —OC(O)$R^{12}$, wherein $R^{12}$ is as defined above. Alternatively, N-hydroxysuccinimide esters, and other activated esters well known in the art, can also be used. Representative examples of preferred acylating agents include, but are not limited to, acetyl chloride, acetic anhydride, propionyl chloride, propionyl anhydride, butanoyl chloride, and the like. When an acyl halide is utilized in this reaction, at least one molar equivalent, based on the acyl halide, of a tertary amine, such as diisopropylethylamine, triethylamine, pyridine and the like, is preferably employed in the reaction to scavenge the acid generated during the reaction.

Preferably, the acylation reaction is conducted at a temperature in the range of about −70° C. to about 70° C. in a diluent that is essentially anhydrous inert under the reaction conditions, such as methanol, ethanol, chloroform, toluene and the like. The reaction is generally complete in about 0.5 to about 24 hours. The oligosaccharide-containing solid support matrix is typically separated from any excess acylating agent by conventional procedures, such as filtration, centifugation and, the like. The matrix is preferably washed one or more times with a suitable diluent, such as water, methanol, ethanol and the like, and dried under vacuum.

C. Pharmaceutical Compositions

The pharmaceutical compositions of this invention comprise an effective amount of an oligosaccharide-containing solid support matrix of the present invention to bind and remove toxin from disease-causing microorganisms from the gastrointestinal tract of a mammalian patient and a pharmaceutically acceptable carrier, wherein the matrix is capable of being eliminated from the gastrointestinal tract. Such pharmaceutical compositions are useful for in vivo treatment of toxin-mediated diseases.

The pharmaceutical compositions preferably comprise from about 0.1 to 99 weight percent of the oligosaccharide-containing solid support matrix and from 1 to 99.9 weight percent of the pharmaceutically inert carrier.

When used for oral administration, which is preferred, these compositions may be formulated in a variety of ways. It will preferably be in liquid or semi-solid form. Compositions including a liquid pharmaceutically inert carrier such as water may be considered for oral administration. Other pharmaceutically compatible liquids or semi-solids, may also be used. The use of such liquids and semi-solids is well known to those of skill in the art.

Compositions which may be mixed with semi-solid foods such as applesauce, ice cream or pudding may also be preferred. Formulations which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The oligosaccharide-containing solid support matrix itself may also be used without the addition of inert pharmaceutical carriers, particularly for use in capsule form.

Doses are selected to provide neutralization of the toxin and elimi-nation of the toxin from the gut of the affected patient. Preferred doses are from about 0.25 to 1.25 micromols of oligosaccharide/kg body weight/day, more preferably about 0.5 to 1.0 micromols of oligosaccharide/kg body weight/day. Using the oligosaccharide-containing matrices of this invention, this means about 0.25 to 1.0 gram matrix/kg body weight/day, which gives a concentration of matrix in the gut of about 20 mg/ml. Administration is expected to be 3 or 4 times daily, for a period of one week or until clinical symptoms are resolved. The dose level and schedule of administration may vary depending on the toxin being absorbed, the particular oligosaccharide structure used and such factors as the age and condition of the subject. Optimal time for complete removal of toxin activity will be be about 1 hour at 37° C., using a concentration of matrix of 20 mg in 1 ml sample As discussed previously, oral administration is preferred, but formulations may also be considered for other means of administration such as per rectum. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain about 1 μmole oligosaccharide/mL.

D. Utility

The oligosaccharide-containing solid support matrices of this invention are useful for neutralizing toxins from disease-causing microorganisms in the gastrointestinal tract of a mammal as well as in diagnostic methods for determining the presence of such toxins in biological samples.

For example, the oligosaccharide-containing solid support matrices may be used to neutralize toxin A from the gastrointestinal tract of a mammal according to the procedures described in U.S. Pat. No. 5,484,773.[4] Thus, in this embodiment, the oligosaccharide attached to the solid support is selected for its ability to bind toxin A. Neutralization is achieved by, for example, the oral administration of an effective amount of the pharmaceutical composition described above.

Similarly, the matrices provided by this invention can be employed to neutralize SLTs expressed by enterohemorrhagic *E. coli* according to the procedures described in Armstrong, et al.[8,9] In this embodiment, the oligosaccharide attached to the solid support is selected for its ability to bind SLTs. Again, neutralization is achieved by, for example, the oral administration of an effective amount of the pharmaceutical composition described above.

Other toxins subject to neutralization as in the manner described above include, for example, cholera toxin, heat labile toxin, and the like.

Additionally, the oligosaccharide-containing solid support matrices of this invention can be utilized to remove toxins from the blood of a mammal by the extracorporeal perfusion of the blood over a column comprising the solid supports and then reintroduction of the blood back into the mammal.

Additionally, the oligosaccharide-containing solid support matrices of this invention are useful for the rapid efficient binding of physiological concentrations of toxins present in biological samples, thus permitting assay of the presence and/or quantity of such toxins in these samples. Typically, the biological sample will be a stool sample. The sample may be extracted and prepared using standard extraction techniques. The sample or extract is then contacted with the oligosaccharide-containing solid support matrix under conditions where any toxin in the sample is absorbed.

The toxin may be measured directly on the surface of the oligosaccharide-containing solid support matrix using any suitable detection system. For example, radioactive, biotinylated or fluorescently labelled monoclonal or polyclonal antibodies specific for the toxin may be used to determine the amount of toxin bound to the support. A wide variety of protocols for detection of formation of specific binding complexes analogous to standard immunoassay techniques are well known in the art.

EXAMPLES

The following examples are set forth to illustrate the claimed invention and are not to be construed as a limitation thereof. Unless otherwise stated, all temperatures are in degrees Celsius. Also, in these examples, unless otherwise defined below, the abbreviations employed have their generally accepted meaning:

CT=chlorea toxin
d=doublet
g=grain
Hz=Hertz
L=liter
LT heat-labile enterotoxin
M=molar
mg=milligram
MHz=megahertz
mL=milliliter
mM=millimolar
μg=micrograms
μL=microliter
μM=micromolar
mmol=millimole PBS=phosphate buffered saline
μm=microns
μmol=micromole
mU=milliunit
TLC=thin layer chromatography
UDP=uridine diphosphate Example 1

Preparation of Solid Support Matrices

Chromosorb P™, commerically available from Manville Corp., Denver, Colo., was silylaminated with 3-aminopropyltriethoxysilane according to the procedure described in Weetal, et al.[16]

To the silylaminated Chromosorb P (20 g) and p-nitrophenyl chloroformate (15 g, 75 mmol) in dry tetrahydrofuran (80 mL) and dry dichloromethane (80 mL), was added diisopropylethylamine (13.1 mL, 75 mmol). The mixture was shaken occasionally for 3 hours and the resulting resin was then filtered, washed with dichloromethane/tetrahydrofuran (1:1, 5×100 mL), and dried under vacuum.

To the resulting dried resin was added 1,6-diaminohexane (8.7 g, 75 mmol) in dry dimethylformamide (200 mL) containing triethylamine (10.5 mL, 75 mmol). The reaction was allowed to proceed for 90 minutes with occasional shaking. The resin was then removed by filtration, washed successively with water (3×300 mL), dimethylformamide (3×300 mL) and dichloromethane/tetrahydrofuran (1:1, 5×100 mL), and dried under vacuum to give 22 g of resin.

A portion of the resin (2.0 g), lactose (27.4 mg, 80 μL) in dry methanol (6.5 mL) was heated to 60° C. in a sealed flask for 47 hours. The mixture was then cooled on ice (~5° C.) and acetic anhydride (2.1 mL) was added. The mixture was shaken occasionally for 12 hours, removed by filtration, and then washed with water (3×50 mL) and methanol (3×50 mL). Fine particles were removed by suspending the resin in methanol and decanting the supernatant until it was clear. Drying the resin under vacuum gave 1.95 g of a lactose-containing solid support matrix. Analysis of the product using the phenol-sulfuric acid assay described in Dubois, et al.[17] indicated an oligosaccharide incorporation of 1.24 μmol/g resin.

Example 1A

Preparation of Solid Support Matrices

A suspension of silylaminated Chromsorb P (20 g, ca. 200 μmole of amine/g) in dry dichloromethane (25 mL) and dry acetonitrile (25 ml,) and p-nitrophenyl chloroformate (40 mg, 200 μmole) and diisopropylethylamine (35 μL, 200 μmol) was shaken for 2 h at room temperature. The solid was collected on a scintered glass funnel and washed with dichloromethane:acetonitrile (1:1; 4×100 mL) and then dichloromethane (100 mL). To a suspension of the residual solid support in dry acetonitrile (50 mL) was then added hexane diamine (58 mg, 500 μmol) and triethylamine (70 μL, 500 μmole) and the mixture was agitated for 1 h. The solid support was then collected on a scintered glass funnel and washed with water (3×300 mL), methanol (2×200 mL) and dichloromethane (2×100 mL).

To the above aminated support (0.5 g) in a slurry with methanol (1.35 mL) was added acetic acid (7 μL) and lactose (8.0 mg, 20 μmol) and the mixture was heated to 60° C. in a sealed flask for 48 h. The mixture was cooled to 5° C. and acetic anhydride (30 μL) was then added and the mixture shaken occasionally for 4 h. The solid support was collected and washed with water (3×20 mL), methanol (3×20 mL) and fine particles were removed by suspending it in methanol and decanting the supernatant until clear. The solid was then washed with dichloromethane (3×20 mL) and dried to afford 0.44 g of solid support. The incorporation of lactose was determined using the assay described by Dubois et al.[17] to be 1.0 μmol/g resin.

Using the procedures of Example 1, the solid support matrices shown in Table I were prepared from the indicated alkylene diamine and oligosaccharide. The chemical structures for these matrices are shown in FIGS. 1–10.

TABLE 1

Solid Support Matrices

Figure 2:
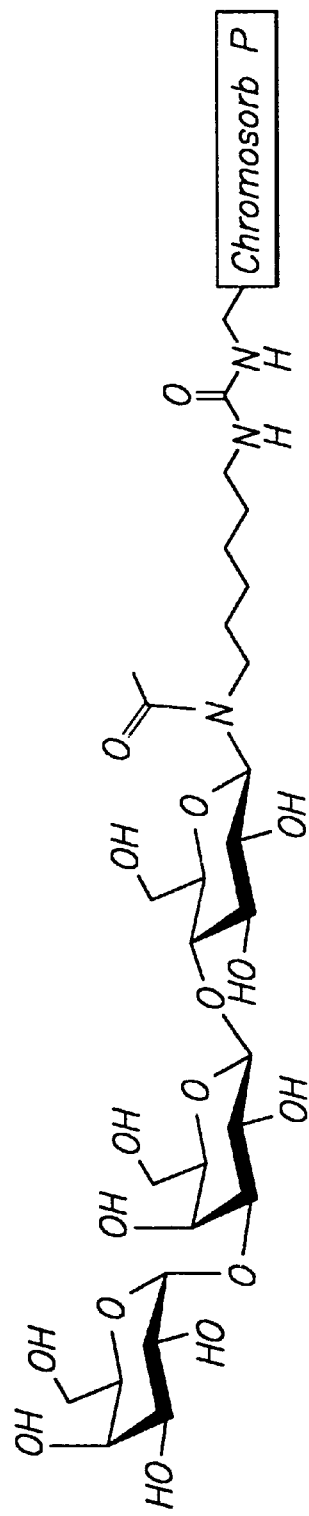
Figure 3:
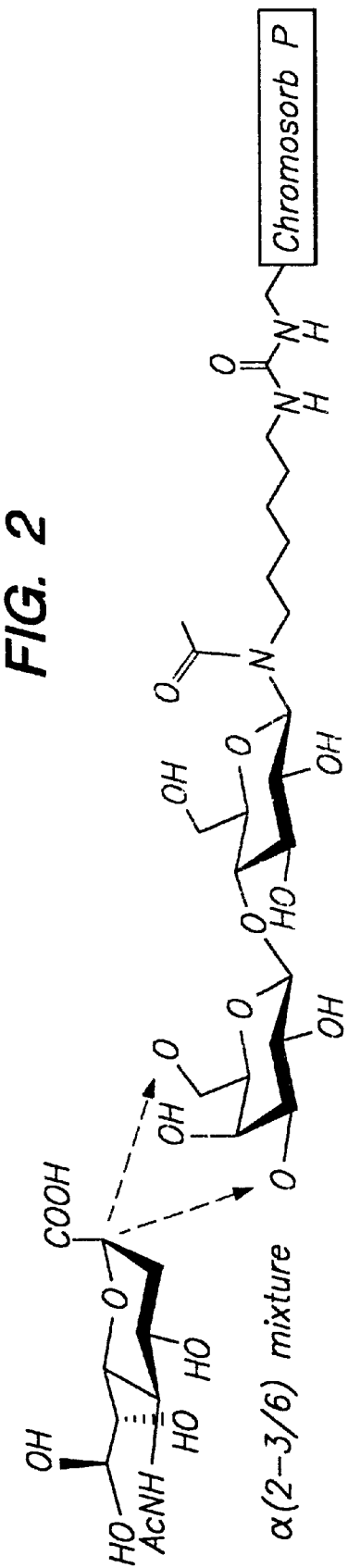
Figure 4:
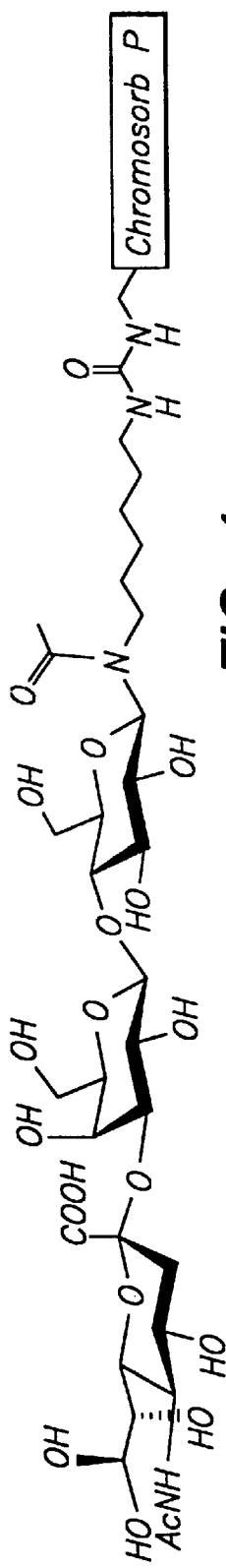
Figure 5:
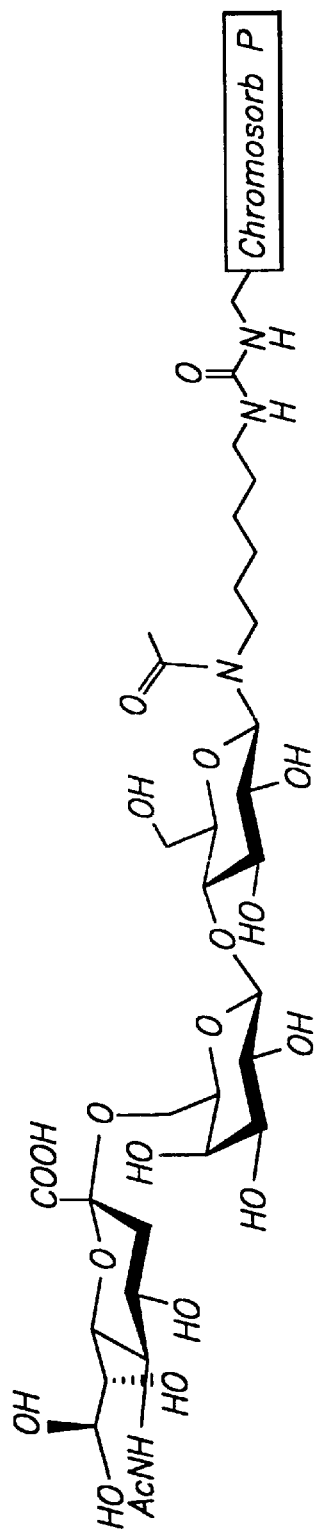
Figure 6:
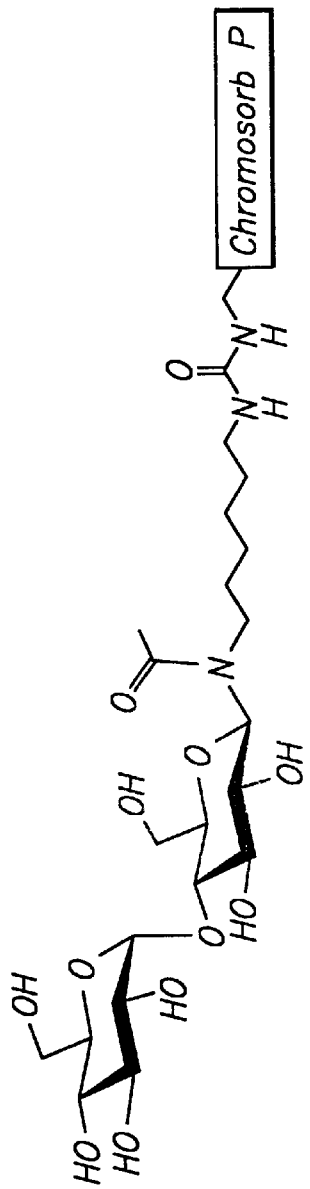
Figure 7:
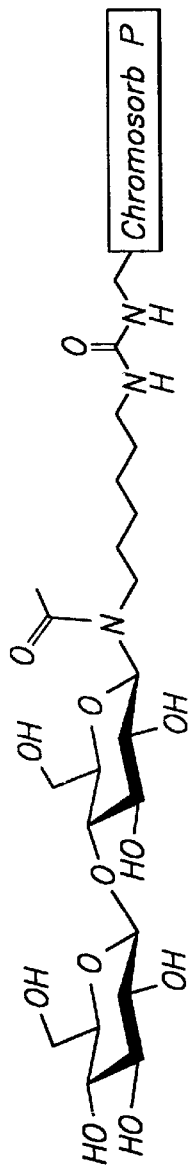
Figure 8:
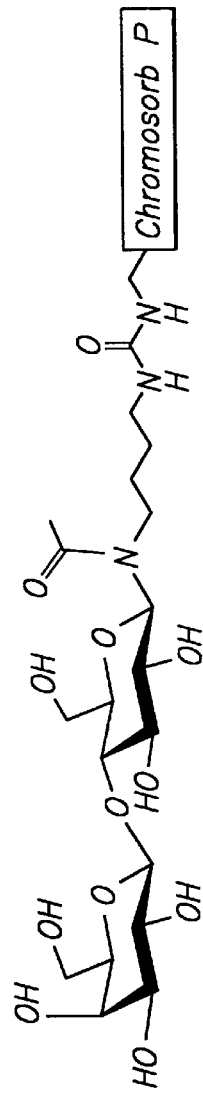
Figure 9:
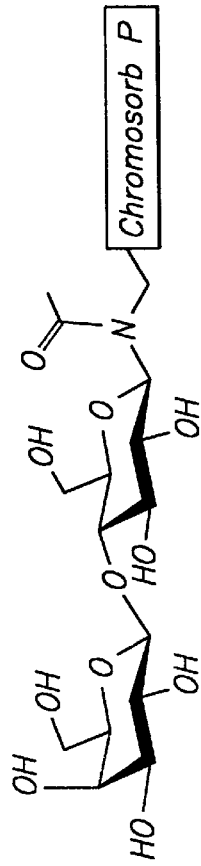
Figure 10:
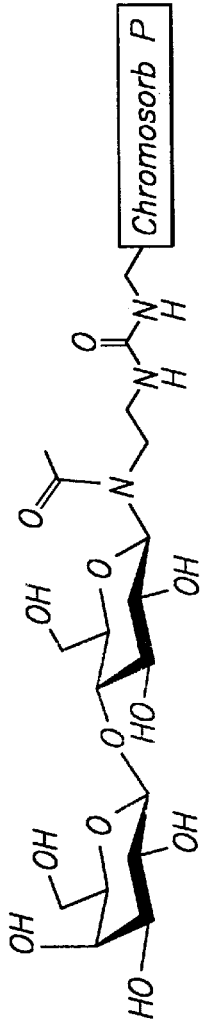

| Example No. | Alkylene Diamine[1] | Oligosaccharide Structure | Oligosaccharide Incorporation[2] |
|---|---|---|---|
| 1 | 1,6-DAH | FIG. 1 | 0.37 |
| 2 | 1,6-DAH | FIG. 2 | 0.64 |
| 3 | 1,6-DAH | FIG. 3 | 1.0 |
| 4 | 1,6-DAH | FIG. 4 | 2.4 |
| 5 | 1,6-DAH | FIG. 5 | 2.1 |
| 6 | 1,6-DAH | FIG. 6 | 2.4 |
| 7 | 1,6-DAH | FIG. 7 | 0.9 |
| 8 | 1,4-DAB | FIG. 8 | 0.8 |
| Comp. A | —[3] | FIG. 9 | 0.98 |
| B | 1,2-EDA | FIG. 10 | 2.6 |

[1]1,6-DAH = 1,6-diaminohexane; 1,4-DAB = 1,4-diaminobutane; 1,2-EDA = 1,2-ethylenediamine.
[2]μMoles per gram of solid support matrix.
[3]No alkylene diamine was used in Comparative Example A. The oligosaccharide was coupled directly to silylaminated Chromosorb P using the procedures described by Blomberg et al.[12,13]

Comparative Example C

SYNSORB 16, as illustrated in FIG. 11, comprises a conventional —O(CH$_2$)$_8$C(O)— linkage. The product had an oligosaccharide incorporation of 0.97 μmol/g.

Comparative Example D

SYNSORB 89, as illustrated in FIG. 12, comprises a conventional —O(CH$_2$)$_8$C(O)— linkage. The product had an oligosaccharide incorporation of 1.0 μmol/g.

Comparative Example E

SYNSORB Cd, as illustrated in FIG. 13, comprises a conventional —O(CH$_2$)$_8$C(O)— linkage. The product had an oligosaccharide incorporation of 1.2 μmol/g.

Example 10

Synthesis of αGal(1-3)βGal(1-4)Glc

α(1-3)-Galactosyltransferase was isolated from calf thymus glands (obtained from Pel-Freeze Biologicals) by extraction and chromatography on a UDP-hexanolamine Sepharose column as described by Blanken and van de Eijnden[18] using sodium cacodylate buffer instead of Tris-maleate buffer. After chromatography the enzyme was concentrated by ultrafiltration, dialyzed against 30 mM sodium cacodylate buffer, pH 6.5, containing 20 mM MnCl$_2$ and 0.1 % Triton X-100 and stored at 4° C. Galactosyltransferase activity was monitored by incubation with 540 μM Galβ(1, 4)GlcNacβ—O—(CH$_2$)$_8$COOCH$_3$, 1 mM UDP-Gal, 35,000 d.p.m. UDP-[$^3$H]-Gal, 1 mg/mL bovine serum albumin, 0.8% Triton X-100, 50 mM MnCl$_2$ and 100 mM sodium cacodylate buffer, pH 6.1 in a total volume of 20 μL. After reaction for 30 minutes at 37° C., products were isolated on a reverse phase C-18 cartridge as previously described by M. M. Palcic, et al.[19]

A reaction mixture containing lactose (50 mg), UDP-Gal (20 mg), α(1-3)-galactosyltransferase (60 mU), alkaline phosphatase (20 U), 20 mM $MnCl_2$ and 0.1% Triton X-100 in 50 mM sodium cacodylate buffer (3 mL) at pH 6.5, was incubated at 37° C. Additional UDP-Gal was added to the mixture after 24 hours (20 mg), and 48 hours (50 mg). After 120 hours, fresh α(1-3)-galactosyltransferase (20 mU) and UDP-Gal (10 mg) were added to the mixture, which was incubated for an additional 72 hours to give about 95% conversion to product. The reaction mixture was filtered through a 0.2 μm Nalgene nylon filter, the filtrate was applied to a Bio-Rad AG 1X8 column (C1-form 2.5×20 cm, 0.6 mL/min) and the column was eluted with water. Saccharide fractions were combined and lyophilized. The dry residue was dissolved in 50 mM potassium phosphate buffer, pH 7.5, β-galactosidase (150 mU) was added to the mixture to destroy unreacted lactose, and the sample left at ambient temperature (24° C.) for 18 hours. The mixture was then boiled for 2 minutes, filtered through a 0.2 μm filter and divided into three portions each of which was loaded onto a C-18 silica gel column (20 g). The columns were eluted with water (200 mL) and the aqueous eluents were concentrated to dryness under reduced pressure. The residue was dissolved in water (5 mL) and applied to a Bio-Gel P-2 column (2.5×100 cm, $H_2O$, 0.2 mL/min). Fractions which contained the trisaccharide were combined and lyophilized to give 10.5 mg of αGal(1-3)βGal(1-4)Glc. $^1H$ n.m.r. data (500 MHz, $D_2O$): δ=5.22 (d, 0.36 H, J 3.6 Hz, H-1α), 5.14 (d, 1 H, J 3.0 Hz, H-1"), 4.66 (d, 0.64 H, J 8.0 Hz, H-1β), 4.51 (d, 1 H, J 8.0 Hz, H-1').

Example 11

Procedure for Screening Solid Support Matrices to Determine Their Ability to Neutralize CT and LT Activity A solution containing purified CT or LT (Sigma Chemical Company, St. Louis, Mo., USA, 2 μg in 1 mL PBS) was added to various solid support matrices (20 mg) in 1.5 mL microcentrifuge tubes and incubated at room temperature for 1 hour on an end-over-end rotator.

After incubation, the matrix was allowed to settle to the bottom of the tubes and the supernatants were carefully removed. Serial five-fold dilutions of the supernatants were prepared and the cytotoxic endpoint determined as described in Example 12 below. The extent of reduction in the endpoint in the presence of the solid support matrix was determined by comparing the endpoint in the presence of the matrix with controls in which the matrix was not added. The results are shown in Table 2.

TABLE 2

Percent Neutralization of LT or CT

| Solid Support Matrix[1] | Toxin | Percent Toxin Activity Remaining |
|---|---|---|
| 1 | LT | 12 |
|   | CT | 20 |
| 2 | LT | N/A |
|   | CT |   |
| 3 | LT | 4 |
|   | CT | 4 |
| 4 | LT | 4 |
|   | CT | 4 |

TABLE 2-continued

Percent Neutralization of LT or CT

| Solid Support Matrix[1] | Toxin | Percent Toxin Activity Remaining |
|---|---|---|
| 5 | LT | 4 |
|   | CT | 1 |
| 6 | LT | 87 |
|   | CT | 100 |
| 7 | LT | 87 |
|   | CT | 100 |
| 8 | LT | 9 |
|   | CT | 9 |
| A | LT | 20 |
|   | CT | 90 |
| B | LT | 15 |
|   | CT | 36 |
| C | LT | 4 |
|   | CT | 20 |
| D | LT | 4 |
|   | CT | 4 |
| Chromosorb P[2] | LT | 100 |
|   | CT | 100 |

[1]Prepared according to the indicated Example No.
[2]Unmodified Chromosorb P.

The data in Table 2 establishes that the solid support matrices of Examples 1–5 were comparable to Comparative Examples B and C in their ability to neutralize either LT or CT activity. These result establish that the differences in linking arm between Examples 1–5 and Comparative Examples B and C do not have any significant affect on toxin binding.

Example 12

Assay of Toxin Activity Using Tissue Culture Cells

The cytotonic activity of CT and LT was measured using Chinese hamster ovary cells (CHO) maintained in Hams F12 medium supplemented with 10% fetal bovine serum (FBS) in an atmosphere of 5% $CO_2$ at 37° C. Toxin samples to be tested were diluted 1:5 in Hams media and filter sterilized through 0.22 μm syringe filter. Samples to be tested were serial 5-fold diluted in media and 100 μL of each dilution was added to wells with confluent monolayers of CHO cells and incubated for 24 hours at 37° C./5% $CO_2$. Each sample was analyzed in duplicate.

Cytotonic effects were readily visible after 24 hour incubation by comparing wells with controls that did not contain toxin. After 24 hours, the cells were fixed with 95% methanol and stained with Geimsa stain. Toxin containing samples from neutralization experiments were treated in an analogous fashion except that the percent neutralization was determined by comparing the endpoint dilutions of samples with and without the solid support matrix.

Example 13

Procedure for Screening Solid Support Matrices to Determine Their Ability to Neutralize Toxin A Activity The purpose of this example is to illustrate the differences between binding of Toxin A with a matrix of this invention (Example 2) compared to a conventional matrix employing a —O($CH_2$)$_8$C(O)— linking arm (Comparative Example D).

Toxin A was purified from a toxin producing strain of C. difficile (ATCC 43255, VPI strain 10463) as described in Heerze, et al.[3] A solution containing purified toxin A (1 mL)

was added to 20 mg samples of various solid support matrices in 1.5 mL microcentrifuge tubes. The tubes were then incubated at room temperature for 1 hour on an end-over-end rotator. After incubation, the solid support matrix was allowed to settle to the bottom of the tubes and the supernatants were carefully removed. Serial two-fold dilutions of the supernatants were prepared and the amount of toxin A activity was determined by measuring the hemagglutination end point using the procedure described in Example 14 below.

The extent of reduction in the end point in the presence of the solid support matrix was determined by comparing the end point with that of controls in which matrix was not added.

Figure 14:
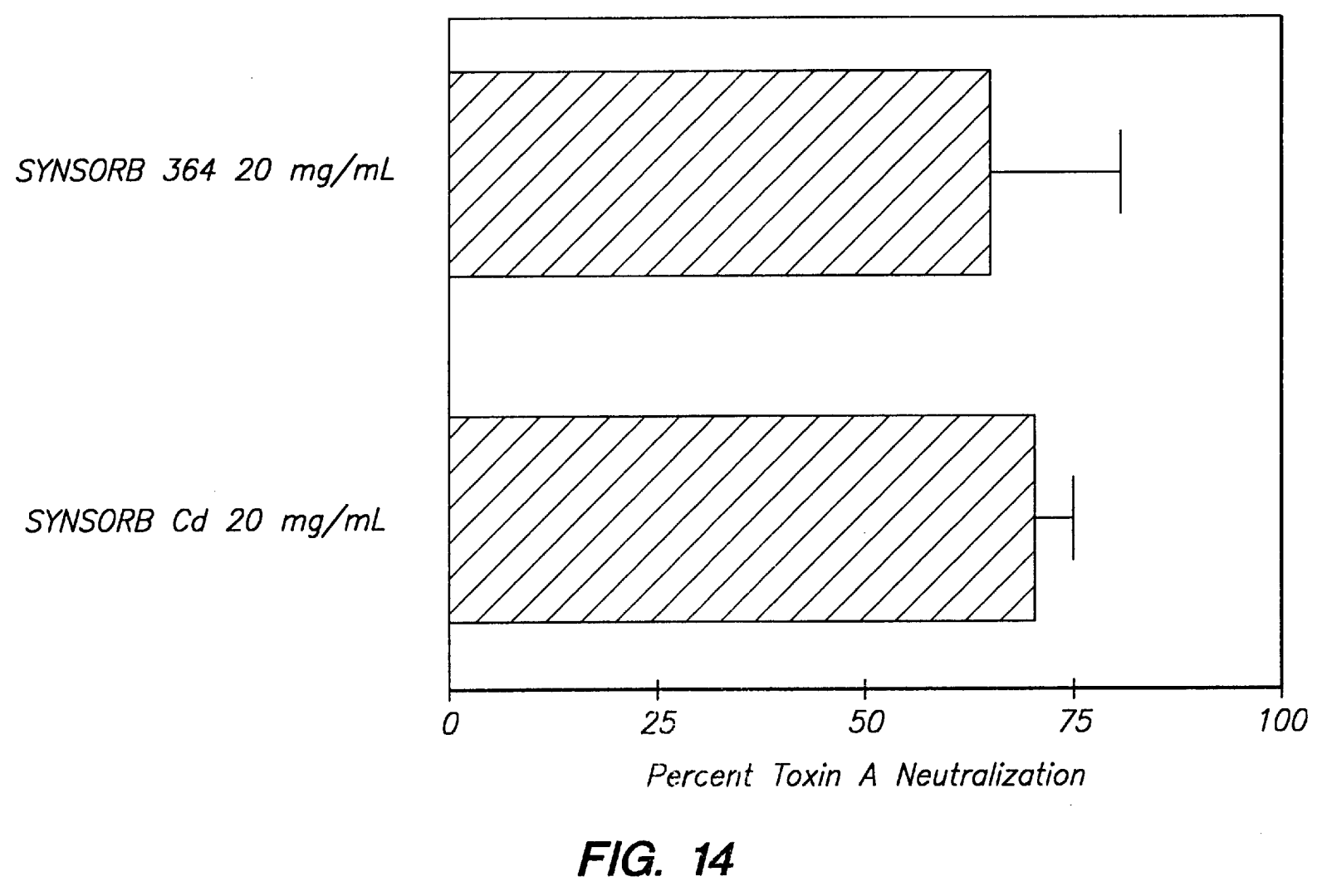

Results are shown in FIG. 14. The data shown in FIG. 14 demonstrate that the solid support matrix of Example 2 was comparable to Comparative Example D in its ability to neutralize toxin A activity.

Example 14

Hemagglutination Assay Using Rabbit Erythrocytes

Fresh rabbit erythrocytes were washed once in PBS and re-suspended at a concentration of 2% (vol/vol) in cold PBS. Serial two-fold dilutions (50 μL) of toxin A-containing solutions were made in cold PBS in U-shaped microtiter wells. An equal volume (50 μL) of rabbit erythrocytes was then added to each well and the microtiter plate was mixed gently. After incubating the plate for 4 h at 4° C., the hemagglutination titer was assessed visually. All assays were done in duplicate.

From the foregoing description, various modifications and changes in the compositions will occur to those skilled in the art. All such modifications coming within the scope of the appended claims are intended to be included therein.

What is claimed is:

1. A solid support matrix of the formula:

$$SS-[R^1-X-\overset{W}{\overset{\|}{C}}-Y(R^2X')_pR^2NR^3-Z]_n$$

wherein SS is a solid support;
$R^1$ is selected from the group consisting of a covalent bond and a hydrocarbylene group having from 1 to about 20 carbon atoms;
$R^2$ is a hydrocarbylene group of from 2 to 20 carbon atoms;
each X' is independently selected from the group consisting of —O— and >$NR^4$ wherein each $R^4$ is independently selected from hydrogen, $R^2NH_2$ or $R^2NR^3Z$ wherein $R^2$ is as defined above;
$R^3$ is selected from the group consisting of hydrogen and —C(O)$R^5$ wherein $R^5$ is selected from the group consisting of hydrogen and hydrocarbyl of from 1 to 20 carbon atoms;
W is selected from oxygen or sulfur;
X is selected from the group consisting of —NH—, —O— and —S—;
Y is selected from the group consisting of —NH—, —O— and —S—;
Z is toxin-binding oligosacchlaride;
p is an integer from 0 to 50; and
n is an integer such that the matrix has a loading level of the toxin-binding oligosaccharide of from about 0.001 to about 2000 μmoles per grain of solid support wherein the total number of atoms separating the solid support from the toxin-binding, oligosaccharide is at least 6.

2. The solid support matrix of claim 1 wherein X and Y are —NH— and W is oxygen.

3. The solid support matrix of claim 2 wherein p is zero.

4. The solid support matrix of claim 3 wherein $R^3$ is selected from hydrogen and —C(O)$CH_3$.

5. A solid support matrix of the formula:

$$SS-[R^1-NH\overset{O}{\overset{\|}{C}}NH-R^6-NR^3-Z]_n$$

wherein SS is a solid support;
$R^1$ is selected from the group consisting of a covalent bond and a hydrocarbylene group having from 1 to about 20 carbon atoms;
$R^3$ is selected from the group consisting of hydrogen and —C(O)$R^5$ wherein $R^5$ is selected from the group consisting of hydrogen and hydrocarbyl of from 1 to 20 carbon atoms;
$R^6$ is an alkylene group of from 4 to 10 carbon atoms
Z is toxin-binding oligosaccharide; and
n is an integer such that the matrix has a loading level of the toxin-binding oligosaccharide of from about 0.001 to about 2000 μmoles per gram of solid support
wherein the total number of atoms separating the solid support from the toxin-binding oligosaccharide is at least 6.

6. A pharmaceutical composition useful for in vivo treatment of a toxin-mediated disease in a mammal, which composition comprises a pharmaceutically acceptable carrier suitable for oral administration and a solid support matrix of the formula:

$$SS-[R^1-X-\overset{W}{\overset{\|}{C}}-Y(R^2X')_pR^2NR^3-Z]_n$$

wherein SS is a solid support;
$R^1$ is selected from the group consisting of a covalent bond and a hydrocarbylene group having from 1 to about 20 carbon atoms;
$R^2$ is a hydrocarbylene group of from 2 to 20 carbon atoms;
each X' is independently selected from the group consisting of —O— and >$NR^4$ wherein each $R^4$ is independently selected from hydrogen, —$R^2NH_2$ or —$R^2NR^3Z$ wherein $R^2$ is as defined above;
$R^3$ is selected from the group consisting of hydrogen and —C(O)$R^5$ wherein $R^5$ is selected from the group consisting of hydrogen and hydrocarbyl of from 1 to 20 carbon atoms;
W is selected from oxygen or sulfur;
X is selected from the group consisting of —NH—, —O— and —S—;
Y is selected from the group consisting of —NH—, —O— and —S—;
Z is toxin-binding oligosaccharide;
p is an integer from 0 to 50; and
n is an integer such that the matrix has a loading level of the toxin-binding oligosaccharide of from about 0.001 to about 2000 μmoles per gram of solid support wherein the total number of atoms separating the solid support from the toxin-binding oligosaccharide is at least 6 and further wherein the matrix is capable of being eliminated from the gastrointestinal tract.

7. The pharmaceutical composition of claim 6 wherein X and Y are —NH— and W is oxygen.

8. The pharmaceutical composition of claim 7 wherein p is zero.

9. The pharmaceutical composition of claim 8 wherein $R^3$ is selected from hydrogen and —C(O)CH$_3$.

10. A pharmaceutical composition useful for in vivo treatment of a toxin-mediated disease in a mammal, which composition comprises a pharmaceutically acceptable carrier suitable for oral administration and a solid support matrix of the formula:

$$SS-[R^1-NHCNH-R^6-NR^3-Z]_n$$
$$\phantom{SS-[R^1-NH}\overset{O}{\|}\phantom{NH-R^6-NR^3-Z]_n}$$

wherein SS is a solid support;

$R^1$ is selected from the group consisting of a covalent bond and a hydrocarbylene group having from 1 to about 20 carbon atoms;

$R^3$ is selected from the group consisting of hydrogen and —C(O)R$^5$ wherein $R^5$ is selected from the group consisting of hydrogen and hydrocarbyl of from 1 to 20 carbon atoms;

$R^6$ is an alkylene group of from 4 to 10 carbon atoms

Z is toxin-binding oligosaccharide; and n is an integer such that the matrix has a loading level of the toxin-binding oligosaccharide of from about 0.001 to about 2000 μmoles per gram of solid support wherein the total number of atoms separating the solid support from the toxin-binding oligosaccharide is at least 6; and further wherein the matrix is capable of being eliminated from the gastrointestinal tract.

\* \* \* \* \*